United States Patent [19]

Lawrence et al.

[11] Patent Number: 6,113,856
[45] Date of Patent: Sep. 5, 2000

[54] METHOD OF MAKING A PH AND AMINE TEST ELEMENT

[75] Inventors: Paul J. Lawrence, Campbell; Peter U. Ly, San Jose; David R. Shockey, Cupertino, all of Calif.

[73] Assignee: Litmus Concepts, Inc., Santa Clara, Calif.

[21] Appl. No.: 09/040,151

[22] Filed: Mar. 17, 1998

Related U.S. Application Data

[62] Division of application No. 08/819,790, Mar. 18, 1997, Pat. No. 5,897,834, which is a continuation of application No. 08/689,758, Aug. 13, 1996, Pat. No. 5,660,790.

[51] Int. Cl.[7] .......................... G01N 33/52; G01N 33/48
[52] U.S. Cl. .......................... 422/58; 436/163; 436/166; 204/433; 210/743; 427/2.13
[58] Field of Search ................... 422/56, 58, 61; 436/163, 168, 166; 204/433, 787.5; 210/743; 427/2.13; 430/221

[56] References Cited

U.S. PATENT DOCUMENTS

| | | |
|---|---|---|
| 3,996,006 | 12/1976 | Pagano . |
| 4,174,292 | 11/1979 | Seidenberger et al. .................. 252/189 |
| 4,194,877 | 3/1980 | Peterson ........................................... 8/4 |
| 4,201,548 | 5/1980 | Tamaoku et al. . |
| 4,793,977 | 12/1988 | Morris . |
| 4,906,249 | 3/1990 | Fogt et al. .................................... 8/647 |
| 4,916,056 | 4/1990 | Brown et al. .............................. 422/56 |
| 5,217,444 | 6/1993 | Schoenfeld . |
| 5,425,377 | 6/1995 | Cailiouette . |

*Primary Examiner*—Lyle A. Alexander
*Attorney, Agent, or Firm*—Townsend and Townsend and Crew LLP

[57] ABSTRACT

Tests for elevated pH and volatile amines in aqueous fluids are disclosed, including tests useful in the diagnosis of bacterial vaginosis and in other biological conditions. By using formulated indicators and indicators held in matrices that are permeable to gas but not to liquid, the tests provide clear and sharp transitions detectable by visual or machine-readable means rather than by subjective judgments such as small gradations in color or olfactory determinations. The tests lend themselves readily to iconic readouts of the test indications and to the inclusion of positive and negative controls.

13 Claims, 5 Drawing Sheets

METHOD OF MAKING A PH AND AMINE TEST ELEMENT

This application is a division of and claims the benefit of U.S. application Ser. No. 08/819.790 filed Mar. 18, 1997 now U.S. Pat. 5,897,834 which is a continuation of U.S. application Ser. No. 08/689,758 filed Aug. 13, 1996, now U.S. Pat. No. 5,660,790 issued Aug. 26, 1997, the disclosures of which are incorporated by reference.

FIELD OF THE INVENTION

This invention relates to test devices for clinical use, and in particular to test devices for conditions characterized by an abnormal pH in an aqueous fluid, and for conditions characterized by the presence of volatile amines. A particular area of interest for the use of these tests is the diagnosis of vaginal diseases.

BACKGROUND OF THE INVENTION

An early study of bacterial vaginosis (BV) involved comparisons of the pH of vaginal fluids of women known to be suffering from BV with those known to be free of the disease. Gardner, H.L., et al., *Am. J. Obstet. Gynecol.* 69:962 (1955). All of the BV positive women in the study were determined to have a vaginal fluid pH greater than 4.5, and 91% of these women had a vaginal fluid pH greater than 5.0. Of the normal (disease-free) women in the test, 92% were found to have vaginal pH between 4.0 and 4.7. The conclusion drawn from the study was that a vaginal pH equal to or greater than 5.0 in conjunction with other clinical criteria was indicative of the presence of BV. Subsequent studies culminating in a report by Amsel, R., et al., *Am. J. Med.* 74:14–22 (1983), resulted in a reduction of the pH threshold for BV to 4.5, and established the remaining criteria as vaginal fluid homogeneity, the whiff test (treatment with alkali followed by an olfactory test to detect for an amine odor), and the presence of clue cells. These are commonly referred to as the Amsel clinical criteria for BV. The conclusion was based on a study group of 397 women in which 81% of BV positive women were found to have a pH greater than 4.5 while only 23% of the normal women were found to have a vaginal fluid pH greater than 4.5.

Studies subsequent to the report by Amsel et al. have now adjusted the pH threshold to 4.7. One of these is the study of Holst, E., *J. Clin. Microbiol.* 28:2035–2039 (1990), in which 100% of the women diagnosed as BV positive by the Amsel criteria were reported to have vaginal fluid pH greater than 4.7. Another is the study by Eschenbach. D. A. *Am. J. Obstet. Gynecol.* 158(4):819–828 (1988), in which all 257 women in the study group who had at least 20% clue cells were shown to have a vaginal fluid pH greater than or equal to 4.7, leading to the conclusion that a threshold value of 4.7 correlated best with the other clinical evidence of BV. Krohn. M. A., et al., *J. Clin. Microbiol.* 27(6):1266–1271 (1989), also verified the correlation between the vaginal fluid pH threshold of 4.7 and the presence of clue cells, and Holmes. K. K., and coworkers further confirmed the pH 4.7 threshold as an indicator of BV—Holmes, K. K., et al., eds., *Sexually Transmitted Diseases*, McGraw-Hill, New York (1990), Chapter 46:527–545 (Holmes. K. K., et al.), and Chapter 47:547–559 (Hillier, S. L., et al.).

Colorimetric tests for elevated vaginal fluid pH have used nitrazine yellow as an indicator. Nitrazine yellow is a monoazo dye that is bright yellow at pH 6.0 and bright blue at pH 7.2, and has a grey-green midpoint at pH 6.6. In the range of interest for testing vaginal fluid, however, which is approximately 3.5 to 6.0, the change occurs in subtle progressions of grey-green that are difficult to interpret.

pH thresholds are useful indicators in diagnosing a variety of other biological conditions, in both humans and animals, and a large number of colorimetric indicators are known and commercially available. Selection of the appropriate indicator is not always a simple task, however, and the choices are often limited, particularly when a specific color change is desired and when stability of the indicator is a consideration.

Normal bovine milk, for example, has a pH of 6.5 to 6.8, and it has been reported (*N. Z. J. Sci. Technol.* 27:258 (1945)) that bovine milk with a pH greater than 6.8 may indicate the presence of bovine mastitis. The difficulties of detecting a pH deviation of such a small magnitude using conventional paper indicator strips are discussed above. A study specifically directed to bovine mastitis was reported in *J. Dairy Sci.* 68: 1263–1269 (1985). The purpose of the study was to determine the suitability of using absorbent blotting paper impregnated with the pH indicator bromthymol blue to test the pH of bovine milk as a method of detecting subclinical bovine mastitis. Milk was added to the indicator-treated paper, and the color of the pH indicator spot was scored on a scale of 1 to 4, where 1 (pale green) was assessed as normal (negative), and 2, 3 and 4 (increasing from moderate green to dark blue-green) were considered abnormal (positive). The pH of the milk was also determined electronically with a carefully calibrated pH meter. The test results illustrated the difficulty in defining accurately the color of the test area: the predictive value of a positive colorimetric test ranged from 49% to 52% (i.e., 51% to 48% of the results were false positives).

As expected, an increase in the test score was accompanied by an increase in the severity of mastitis as defined by other diagnostic measures. However, in milk from animals with less severe mastitis. the considerable overlapping of results "highlighted the possible error in interpretation of indicator scores. The wide variation of milk pH [as determined electronically] within each BTB [Brom Thymol Blue color] score showed that the indicator results were not closely related to pH." The investigators stressed the importance of using color comparators which resemble as closely as possible the actual pH test method being utilized. If the colorimetric milk pH test results were to be interpreted immediately, it was important to use comparators that were also wetted with milk. If the colorimetric pH test results were to be determined after the milk spots had dried, it was advantageous to use dry comparators.

Returning to bacterial vaginosis, the whiff test, which is one of the Amsel criteria, originated in a study by Pheifer, et al., *N. Engl. J. Med.* 298:1429–1434 (1978), that reported the presence of a characteristic fishy amine odor upon the addition of 10% KOH to a vaginal fluid specimen from a woman with BV. The odor is caused by the alkaline volatilization of amine salts found in the vaginal fluid of women with BV. Unfortunately, the test is highly subjective, it exposes the health care worker to potential biological hazards, and it is disagreeable and vulnerable to error, since it is performed on a microscope slide which, due to the transient nature of the amine odor, must be placed directly under the nose and sniffed immediately after the addition of the KOH.

Alternatives to the whiff test are analytical procedures such as high voltage electrophoresis (Chen, K. C .S., et al., *J. Clin. Invest.* 63:828–835 (1979)), thin-layer chromatography (Chen, K. C. S., et al., *J. Infect. Dis.* 145:337–345

(1982), and Sanderson, B. E., et al., Br. *J. Vener. Dis.* 59:302–305 (1983)), gas chromatography (Gravett, M. G., et al. *Obstet. Gynecol.* 67:229–237 (1986), and Dravenieks, A., et al., *J. Pharma. Sc.* 59:495–501 (1970)), and high-performance liquid chromatography (Cook, R. L., et al., *J. Clin. Microbiol.* 30:870–877 (1992)). These procedures, although more accurate and reliable than the whiff test, are expensive, time-consuming, and not suitable for on-site testing in a physician's office or clinic.

Clue cells, which constitute a further Amsel criterion, are independently correlated with BV, and in the hands of a skilled microscopist are a very sensitive and specific indication of this infection. Clue cells are squamous vaginal epithelial cells found in vaginal fluid when BV is present. The cells are covered with numerous bacteria, giving them a stippled or granular appearance, and their borders are obscured or fuzzy because of the adherence of numerous rods or cocci. According to standard clinical practice, a diagnosis of BV is established when at least 20% of the detectable epithelial cells are clue cells. Holmes, et al., *Sexually Transmitted Diseases*, 2d ed., McGraw-Hill, Inc., New York, 1990.

Distinguishing between true clue cells in which the adherent bacteria completely obscure the edges of the cells and cells with simply a few adherent bacteria requires training and experience. One source of error is similarity in appearance between clue cells and trichomonads. white blood cells and other vaginal fluid components, frequently resulting in an incorrect identification of these cells as clue cells, and therefore false positive test results. Another is that clue cells when present are frequently obscured by numerous vaginal fluid components causing the clinician to miss the clue cells completely or to quantify them at levels below their actual level. This can result in a false negative test result. Therefore, it would be highly desirable to have a distinct anaslyte that is accurately and conveniently monitored and whose presence is correlated with clue cells.

SUMMARY OF THE INVENTION

The present invention resides in several discoveries, of value both by themselves and in specific applications including their use in the diagnosis of vaginal infection.

One of these discoveries lies in a method for formulating a pH indicator of the type that contains both an ionizable phenol group and a negatively charged group, and in pH indicators formulated in this manner. According to this discovery, an indicator of this type can be immobilized in a solid polymer matrix containing quaternary ammonium groups with two useful results:

(1) the indicator will remain immobilized in the matrix when wetted with an aqueous liquid sample, i.e., the indicator will resist bleeding out of the matrix or into adjacent areas of the matrix; and (2) the transition point of the indicator, i.e., the pH at which a visible color change occurs, is lowered to a degree depending on the density of quaternary ammonium groups in the polymer and the ratio of the polymer concentration to the indicator concentration, and is sharpened to cause the transition to occur over a narrower range of pH. Thus, indicators can be adjusted to undergo transitions at selected pH values, increasing the range of indicators suitable for any selected transition point and enabling one to select a preferred indicator and adapt it for a particular use.

A related discovery is a test device for analyzing an aqueous liquid sample (usually a biological specimen) for a pH equal to or greater than a critical point in the range of 4.6 to 4.8 (preferably about 4.7) by a detectable transition, in combination with a positive control that shows a similarly detectable transition at a lower pH, the two changes being independently visible on the test device. The positive control is useful in assuring that the indicator is not malfunctioning for reasons such as manufacturing error in the device, and that the device has been exposed to sufficient sample to produce a reading if the sample were indeed positive. In preferred embodiments, the test device also contains a negative control, independently visible, that includes indicator whose change is caused not by application of a sample but by the decomposition or deterioration of the indicator itself.

A further discovery is a test device for detecting salts of volatile amines in an aqueous liquid sample (again, usually a biological specimen). This device contains a dry, solid gaseous amine-releasing substance in addition to an amine indicator retained in a matrix that is impermeable to aqueous liquids. The gaseous amine-releasing substance eliminates the need for the operator of the test to handle aqueous alkali. A related discovery is that this test when performed on a specimen of vaginal fluid serves as a reliable indication of the presence of clue cells in the vaginal fluid, avoiding the need to microscopically observe and count clue cells.

A still further discovery is a test device that combines the test for pH at or above the critical point quoted above and the test for salts of volatile amines in a single aqueous liquid sample, with independent visual indications. This device is of particular utility in the diagnosis of bacterial vaginosis. A related discovery is that this device can be used to test for two of the four tests in the Amsel criteria for bacterial vaginosis. A further related discovery is that the tests in this device can be used by themselves as a means for diagnosing bacterial vaginosis, without the two additional criteria of the Amsel test.

As explained in detail below, one implementation of the concepts of this invention is a combination test device for BV in vaginal fluid that shows a sharp visual transition at pH 4.7, and provides a reliable visual indication of the presence of amines indicative of BV. A particularly preferred pH indicator is nitrazine yellow which, when in combination with quaternary ammonium groups, changes directly from greenish-yellow to blue over a narrow pH range of approximately 0.1 pH units as the pH rises, the transition centering around pH 4.7. The independently visible positive control changes color at a lower pH encountered when any specimen of the fluid is applied, regardless of whether or not BV is present. The two transitions are independently visible such that the occurrence of both indicates a pH of 4.7 or higher, while the occurrence of only the lower-pH transition (the positive control) indicates a pH below 4.7. The two transitions can be arranged in a geometric pattern that serves as an indication of the result. A particularly preferred pattern is a pair of orthogonal bars forming a plus sign, the horizontal bar containing the indicator that changing color at low pH and the vertical bar containing the nitrazine yellow and quaternary ammonium groups. A specimen with a pH below 4.7 thereby produces a minus sign by creating a color change in the horizontal bar only, while a specimen with a pH above 4.7 produces a plus sign by creating color changes in both horizontal and vertical bars. The background area serves as the negative control.

The amine test differentiates between amines volatilized by alkali and those that are not volatilized by alkali by incorporating solid alkali accessible to the specimen, an indicator accessible to a liquid specimen, and an indicator accessible only to vapors emitted by the specimen, in the same device. Thus, the specimen is first contacted with the solid alkali, then applied to both indicators, one of which will undergo a color change regardless of the presence or absence of volatile amines, and the other a color change only in the presence of volatile amines. As in the pH test, the two indicators can be arranged in a geometric pattern, preferably one in the form of an icon that symbolizes the result in a readily recognizable manner. Like the pH test, a pair of orthogonal bars can be used, with the indicator that is accessible to liquid residing in a horizontal bar (the positive control) and the indicator that is accessible only to vapor residing in a vertical bar crossing the horizontal bar. A specimen without volatile amines thus produces a minus sign by causing a color change in the horizontal bar only, while a specimen with volatile amines produces a plus sign by causing a color change in both horizontal and vertical bars. The background field surrounding both bars serves as the negative control. Preferred test devices include both the pH test and the amine test in separate areas of the device. A single specimen is applied to the two test areas separately, preferably the pH test first and the amine test second.

These and other features and advantages of the invention and its preferred embodiments will be more readily understood by the descriptions that follow.

BRIEF DESCRIPTION OF THE DRAWINGS

FIG. 5b is an enlarged and exploded side view of the test card of FIG. 5a.

Figure 1:
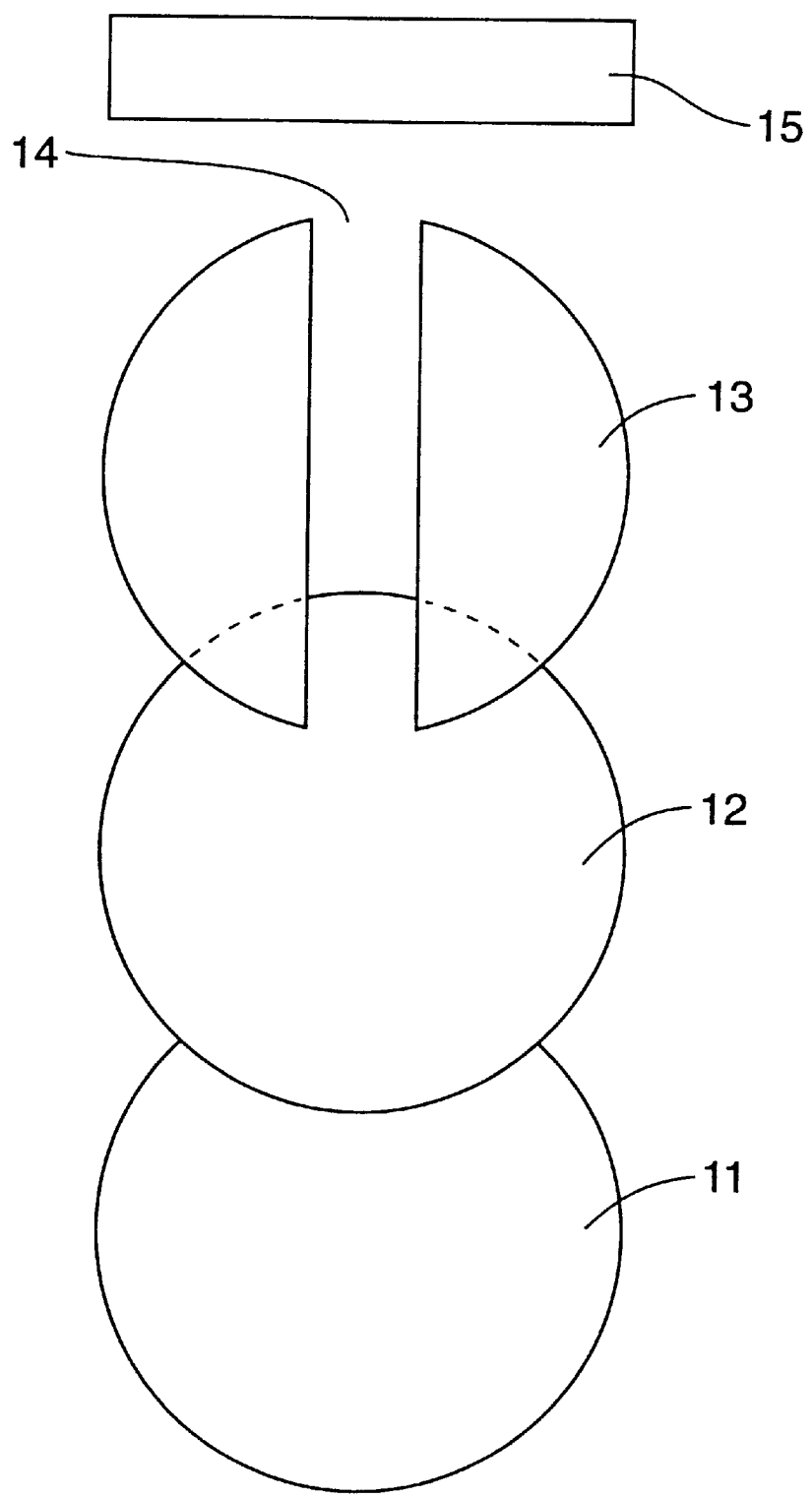
FIG. 1 is a plan view of each of several laminae in one example of a pH test element in accordance with this invention, the laminae shown separately in the order in which they are applied.

DETAILED DESCRIPTION OF THE INVENTION AND PREFERRED EMBODIMENTS pH Formulations and Tests pH indicators with ionizable phenol groups and negatively charged groups are many and varied. Preferred negatively charged groups are sulfate and sulfonate groups. Examples of indicators with ionizable phenol groups and negatively charged groups are:

acid blue 92 (anazolene sodium, CAS No. 3861-73-2)

acid blue 29 (CAS No. 5850-35-1)

acid alizarin violet N (CAS No. 2092-55-9)

bromophenol blue (3',3",5',5"-tetrabromophenolsulfonephthalein, CAS No. 155-39-9)

bromochlorophenol blue (3',3"-dibromo-5',5"-dichlorophenolsulfonephthalein, CAS No. 102185-52-4)

bromocresol green (3',3",5',5"-tetrabromo-m-cresolsulfonephthalein, CAS No. 76-60-8)

chlorophenol red (3',3"-dichlorophenolsulfonephthalein, CAS No. 4430-204)

bromocresol purple (5',5"-dibromo-o-cresol sulfonephthalein, CAS No. 115-40-2)

alizarin complexone dihydrate ((3,4-dihydroxy-2-anthraquinolyl)methyliminodiacetic acid, CAS No. 3952-78-1)

alizarin red S monohydrate (3,4-dihydroxy-9,10-dioxo-2-anthracenesulfonic acid, sodium salt, CAS No. 130-22-3)

bromothymol blue (3',3"-dibromothymolsulfonephthalein, CAS No. 76-59-5)

brilliant yellow (CAS No. 3051-11-4)

phenol red (phenolsulfonephthalein, CAS No. 34487-61-1)

cresol red (3',3"-dimethylphenolsulfonephthalein, CAS No. 1733-12-6)

m-cresol purple (2',2"-dimethylphenolsulfonephthalein, CAS No. 2303-01-7)

thymol blue (2',2"-dimethyl-3',3"b-diisopropylphenolsulfonephthalein, CAS No. 76-61-9)

nitrazine yellow (2-(2,4-dinitrophenylazo)naphthol-3,6-disulfonic acid, disodium salt, CAS No. 5423-07-4)

All of these indicators are readily available from commercial suppliers. Preferred indicators are bromophenol blue, bromochlorophenol blue, bromocresol green, bromocresol purple, bromothymol blue, brilliant yellow, and nitrazine yellow.

The quaternary ammonium groups in the polymer can be any groups capable of asserting a positive charge sufficient to form an ionic attraction with the negatively charged group(s) in the indicator. Preferred quaternary ammonium groups are lower alkyl ammonium groups in which the alkyl groups are $C_1$–$C_4$ alkyl groups. Trimethylammonium groups are particularly preferred. The quaternary ammonium groups are believed to facilitate the deprotonization of the ionizable phenol, causing the deprotonization and hence the color change to occur at a lower pH and to occur less gradually (i.e., in a narrower transition zone) as the pH rises.

The quantity of quaternary ammonium groups in the polymer formulation can vary widely, depending on how far the color transition point is to be lowered and the degree of sharpening desired for the transition. In many applications of this invention, the amount of quaternary ammonium groups will be selected to lower the mid-range transition point of the indicator by about 1.0 to about 3.0 pH units, and preferably by about 1.5 to about 2.5 pH units, with about 2.0 pH units preferred. The amount of quaternary ammonium groups can also be expressed in terms of the alkali value of the resulting polymer. This value represents the milligrams of KOH equivalent to the basicity of the quaternary ammonium groups contained in 1 g of the dry polymer. In most implementations of this invention, the alkali value will range from about 5 to about 50, with values ranging from about 15 to about 40 preferred.

In preferred embodiments, the quaternary ammonium groups are bound to a polymer that is porous (or otherwise water-permeable) and hydrophilic and thereby permeable to aqueous liquid specimens. The hydrophilic character of the polymer is due either to the presence of the quaternary ammonium groups or to other groups on the polymer structure. The polymer itself can be any polymer which is inert relative to the components of the specimen being tested, and which is solid and can be formed into a thin layer, coating or lamina. The polymer should be insoluble in aqueous media in general, and in vaginal fluid for those embodiments of the invention that are designed for testing vaginal fluid. Examples of suitable polymers are transparent polymers such as acrylic polymers, particularly copolymers of acrylic and methacrylic acid esters, and diethylaminoethyl cellulose. Two presently preferred polymers that are readily available from commercial suppliers are EUDRAGIT® RL PO and EUDRAGIT® RS PO Ammonio Methacrylate Copolymers, which are copolymers of methyl, ethyl and trimethylammonioethyl esters of acrylic and methacrylic acids, as chloride salts. The quaternary ammonium groups are present on these polymers as trimethylammonioethyl esters of methacrylate units that constitute 10.4% (RL PO) or 5.6% (RS PO) by weight of the polymer. The alkali values are 28.1 and 15.2, respectively. These polymers are available from Rohm Tech Inc., Maiden, Mass., USA.

The use of nitrazine yellow as the indicator and the trimethylammonioethyl esters of EUDRAGIT RL PO can serve as an example. The transition point of nitrazine yellow in the absence of quaternary ammonium groups is about pH 6.6. By varying the relative amounts of nitrazine yellow and this particular polymer, one can lower the transition point by a selected amount. Applying the polymer-indicator mixture as a liquid solution of which the polymer constitutes 25.0% by weight and the indicator constitutes varying amounts ranging from 0.1% to 0.6% by weight, the transition point of the indicator will be lowered to pH 4.7 at nitriazine yellow concentrations of 0.2% and 0.34%, to pH 4.4 at 0.36%, to pH 4.3 at 0.4%, and to pH 4.2 at 0.6%.

In general, best results will often be obtained within certain ranges of the ratio of indicator to quaternary ammonium groups. For nitrazine yellow and EUDRAGIT RL PO, the ratio, expressed as the weight ratio of KOH equivalent in the polymer to nitrazine yellow, has a preferred range of about 1.0 to about 6.0, and a more preferred range of about 1.5 to about 3.5. For EUDRAGIT RL PO, a preferred weight ratio range of polymer to nitrazine yellow is about 50 to about 250, and more preferably about 75 to about 125. In terms of a liquid solution of the same polymer and indicator to be applied to the foundation lamina, a preferred range of the polymer in the solution is about 12% to about 35%, and a preferred range of the nitrazine yellow is about 0.05% to about 1.0%, all by weight.

In test devices in accordance with this invention, the polymer and indicator form a solid thin, and preferably homogeneous and transparent, water-permeable layer (that can be referred to as a pH indicator lamina) that remains solid and intact (i.e., does not dissolve or disintegrate into powder) when saturated with aqueous liquids. Additional components can optionally be included in this pH indicator lamina, or in the composition from which it is formed, for a variety of purposes. Examples of such components are a vehicle for spreading or applying the lamina components to a surface, drying agents, penetrants, agents to facilitate wetting of the polymer by the sample, and agents to facilitate depositing or adhering the mixture on the surface of a solid support. Still other optional components and the reasons for including them will be readily apparent to those skilled in the art. Typical of these added components are low molecular weight alcohols, penetrants, and surface active agents. Sorbitol is one example of a suitable penetrant.

As suggested above, the pH indicator lamina can be formed over the surface of a support substrate or foundation lamina, for stability of the lamina and ease of manufacture. A typical example is a polyethylene terephthalate film such as MYLAR® (Du Pont de Nemours & Co., Wilmington, Del., USA), which can be coated with ethyl cellulose or a similar coating to improve the adherence of the pH indicator lamina components to the solid support.

In preferred test devices in accordance with this invention, the indicator that has been modified to change color at the desired transition point will occupy one geometric region on the device, while an indicator in another geometric region will change color at a pH lower than the first by at least about 0.7 pH unit. A color change in this second region when contacted with a liquid whose pH lies between the transition points of the two regions will inform the user that the indicator in the second region is in functional condition, and this information is logically extended to both indicators in the device. The second region thus serves as a specimen-activated positive control lamina, i.e., one that would show a color change upon application of a specimen regardless of whether the pH of the specimen was above or below the transition point of the test. The color change in the positive control region would thus indicate that the indicator in the test region (i.e., the pH indicator lamina) would also show a color change if the pH were high enough to exceed the transition point, and that sufficient sample was applied to wet the surface of the device. Using a pH indicator lamina with nitrazine yellow adjusted to a transition point of pH 4.7 and vaginal fluid as an example, the positive control lamina will preferably contain an indicator having a transition point at a pH that is 0.7 or more pH units below 4.7, more preferably one whose transition point lies at a pH of 4.0 or below, and most preferably at a pH of 3.5 or below. It is particularly preferred that the color change be the same or similar to the color change undergone by the indicator changing at pH 4.7.

An example of an indicator that is useful for the positive control when the pH indicator lamina has a transition point of 4.7 is a mixture of nitrazine yellow and bromocresol green. The weight ratio of nitrazine yellow and bromocresol green in such a mixture can vary and different ratios will produce different transition points. In general, however, best results will be obtained with a weight ratio (bromocresol green to nitrazine yellow) of about 0.05 to about 20.0, and preferably from about 0.5 to about 5.0. This indicator or indicator combination can likewise be immobilized in a water-permeable polymer, and the same polymer impregnated with the pH 4.7 indicator can be used for the lower-pH indicator as well, although the invention is not restricted to devices utilizing the same polymer in both locations. When the polymer and indicators are applied as a liquid solution, the preferred amounts of the indicators in the solution are from about 0.05% to about 1.0% by weight each.

The indicators (i.e., the pH indicator lamina and the positive control lamina) are preferably arranged on the test device so that the two color changes are independently visible, and it is further preferred that the device include a third indicator region that remains visible but protected from the specimen so that application of the specimen itself does not cause this indicator to change color. This non-changing region thus serves as a negative background control, since any deviation from its original color indicates that the indicator itself has decomposed or has otherwise undergone a chemical conversion adverse to its effectiveness in the test, or has a defect incorporated in it during the manufacturing stage, or that an inadequate amount of sample has been applied.

Figure 2A:
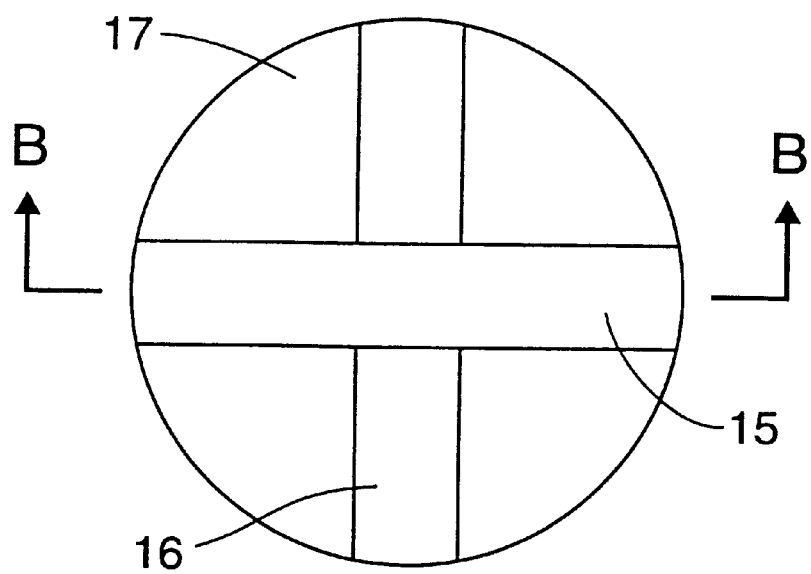
FIG. 2a is a plan view of a laminate formed from the laminae of FIG. 1.
Figure 2B:
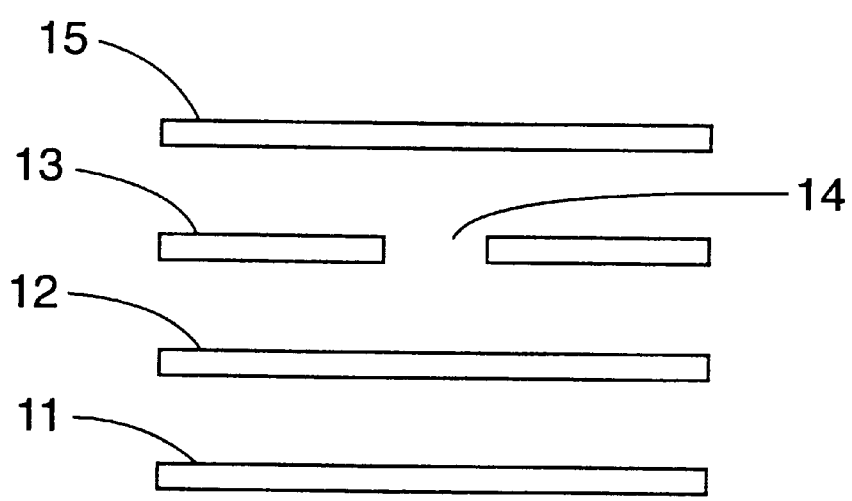
FIG. 2b is a cross section of the various laminae of FIG. 2a, taken along the line B—B thereof.

As indicated above, a preferred configuration of the indicators is two crossed bars forming a plus sign. FIGS. 1, 2a, and 2b illustrate a laminate having this configuration. A foundation lamina 11 supports the pH indicator lamina 12 (whose transition point is pH 4.7) toward the lower surface of the device. An intermediate or liquid-channeling lamina 13 is applied over the pH 4.7 indicator lamina, the liquid-channeling lamina being transparent and impermeable to liquid but having an elongated gap 14 in its center in the form of a vertical bar that permits the passage of liquid and forms the vertical bar of the plus sign. The positive control lamina 15 (with the lower-pH indicator) is then applied over the intermediate lamina in the form of a bar that serves as the horizontal portion of the plus sign.

A specimen applied to the entire upper surface of the device thus wets the entire positive control lamina and passes through and around it to the intermediate lamina which permits penetration only through the gap, thereby reaching the underlying pH 4.7 indicator lamina only on the region 16 beneath the gap. Any color change in the pH 4.7 indicator is restricted to the vertical bar 16 region under the gap. The remainder of the pH 4.7 indicator lamina 17 (the area surrounding the plus sign) is protected from the specimen and thus does not change color. Vaginal fluid specimens that have pH less than 4.7 will produce a minus sign on the device (only the positive control indicator bar 15 will be visible), while specimens with pH 4.7 or greater will produce a plus sign (both bars 15 and 16 visible).

By using the most basic and fundamental concepts of this invention, pH test devices are prepared that are capable of determining whether the pH of an aqueous liquid sample exceeds a selected threshold value by a color change in a defined geometric region of the device, while immobilizing the indicator on the device so that the indicator does not migrate when wetted by the sample, and while modifying the indicator so that it undergoes a transition within a relatively sharp pH range. The threshold value is selected first by selection of the indicator, and second by adjustment of the transition point of the indicator by the incorporation of quaternary ammonium groups in the matrix. Aqueous liquids that can be tested by this device include aqueous solutions as well as suspensions and emulsions in which the continuous phase is water or an aqueous solution. Although aqueous liquids from any source can be used, the invention will be of primary interest in biological fluids, such as urine, saliva, blood, and vaginal fluid. In vaginal fluid, as indicated above, a prime example of the use of this invention is in the detection of bacterial vaginosis. Vaginal fluid can also be tested for other purposes by this invention, such as for example for the pH change (a rise from 4.5 to 7.0 and higher) accompanying the rupture of the amniotic membrane. The invention will be of interest not only in testing human fluids, but also fluids from animals, such as livestock and pets. One example is the detection of mastitis in cattle by determining whether the pH of the milk has reached or surpassed a threshold value of approximately 6.8.

Amine Test

Like the pH test device of this invention, the amine test device, or the amine test portion of a test device that combines both tests, is a laminated structure. Individual laminae in the structure perform distinct and complementary functions, the laminae collectively coacting to provide an accurate and reproducible test whose results are read entirely by visual indications. Two key laminae are a solid gas-releasing lamina immediately accessible to the fluid specimen and a gas-permeable indicator lamina that is permeable to gas and impermeable to the aqueous liquid specimen itself or to any of its components that are not in gaseous form. The gas-releasing lamina is a solid lamina of alkali that reacts with amine salts in the specimen and converts them to volatile amines. The volatilized amines then penetrate the gas-permeable indicator lamina where they cause a color change in the indicator.

The terms "volatile amines" and "volatilized amines" include amines that are only slightly volatile as well as those that are sufficiently volatile to escape into the atmosphere at substantial rates. Slightly volatile amines are those that form only a thin film of gas at the liquid surface without significant amounts diffusing into the atmosphere. This thin film of gas however is sufficient to penetrate the gas-permeable indicator lamina.

The choice of solid alkali for the gas-releasing lamina is not critical and can vary. In general, alkali and alkaline earth metal aluminates, carbonates and hydroxides can be used. Best results will most often be achieved with the use of either sodium aluminate, sodium carbonate, or magnesium hydroxide. Sodium aluminate is particularly preferred.

Permeability only to gas in the gas-permeable indicator lamina can be achieved in a variety of ways, depending on the nature of the sample. A convenient method for aqueous specimens is the use of a porous hydrophobic polymer. Suitable polymers are those that are solid, insoluble in aqueous fluids, particularly vaginal fluid, and readily formed into a layer, coating or lamina that does not dissolve, disperse into particulate form, or otherwise disintegrate upon contact with these fluids. Examples of such polymers are ethyl cellulose, cellulose acetate and cellulose nitrate. Ethyl cellulose is particularly preferred. Alternatively, the indicator can reside in a hydrophilic water-permeable polymer that is covered by a hydrophobic lamina.

Any indicator that changes color upon exposure to amines, and preferably amines in a fluid specimen that would otherwise be acidic, may be used. Bromocresol green is one example, and may be used here as well as in the pH test. Other examples are bromophenol blue, bromocresol purple, bromochlorophenol blue, nitrazine yellow, and various other indicators among those listed above.

The gas-releasing lamina and the gas-permeable indicator lamina are arranged in the test device such that contact between the alkali in the gas-releasing lamina and the indicator in the gas-permeable lamina does not occur in the absence of a fluid specimen. The arrangement is such to permit the user to first contact the gas-releasing lamina with the specimen (preferably using a swab), and then contact the gas-permeable indicator lamina with the same specimen, so that gas present in the specimen will penetrate the gas-indicator lamina.

The gas-permeable indicator lamina may thus be the lowermost lamina in the device, furthest away from the surface to which the specimen is applied, and the last lamina to be influenced by the specimen. This lamina can optionally be applied over a foundation or support lamina, as in the pH indicator lamina. With the use of polymer such as ethyl cellulose as the lamina matrix, however, the lamina is structurally stable and reliable in performance without the use of an underlying foundation lamina.

In addition to the arrangement of these two laminae relative to each other, the generation of the volatile amines by the device and the penetration of these amines to the indicator is enhanced by the use of intervening laminae which can also serve to define geometrical regions where the color change will occur, plus the same types of information as provided by the pH test.

As in the pH test, the color change in the amine test is preferably arranged in such a manner that it causes a particular geometric indicium to appear that is otherwise invisible. One means of achieving this is to restrict the access of the volatile amines to a defined geometrical region in the gas-permeable indicator such that the remaining regions of the lamina are still visible. This can be achieved by applying a gas-channeling lamina directly over the gas-permeable lamina, the gas-channeling lamina being light-transmissive or transparent and made of a gas-impermeable material except for an opening or passage within its borders. The volatile amines are thereby channeled through the opening, and the only portion of the gas-permeable indicator lamina that shows a color change is the area directly underneath the opening. Examples of light-transmissive materials that are impermeable to gas are various polymers, particularly polyamides, polyacrylates, shellacs and varnishes.

As further protection of the indicator in the gas-permeable lamina from liquid amines, a lamina that is permeable to gas but impermeable to liquid can be placed directly over the gas-channeling lamina. For convenience, this protective lamina may be constructed of the same polymer used in the gas-permeable indicator lamina. Here again, ethyl cellulose is preferred.

A second indicator region can be included in the amine test device to respond to the presence of the specimen regardless of whether or not there are volatile or volatilizable amines present in the specimen. As in the pH test, this second indicator region serves as a specimen-activated positive control, and can be applied as a further lamina designated a positive control lamina. The indicator in this lamina can be immobilized in a matrix that will permit the penetration of the fluid sample, and the indicator itself can be any indicator that will change color upon application of the sample. The color change may be due to the nonvolatile amines in the sample, or to the solid alkali in the gas-releasing lamina as the alkali is drawn into the sample by the applicator swab. The immobilizing matrix can be a hydrophilic polymer, and prominent examples are the same polymers cited above as preferred for use in the pH indicator lamina of the pH test. The indicator can be the same indicator used in the gas-permeable indicator lamina, although any indicator producing a color change upon contact with the specimen can be used.

As in the pH test, the two indicators (i.e., the indicator accessible only by volatilized amines and the indicator in the positive control lamina which is accessible by both volatilized and nonvolatilized amines as well as the alkalinized sample) are arranged so that the two color changes are independently visible. It is further preferred that the device include a third indicator region that remains visible but protected from the specimen so that it does not change color under any circumstances. This non-changing region thus serves as a negative background control for the same reasons as the negative control in the pH test.

Figure 3:
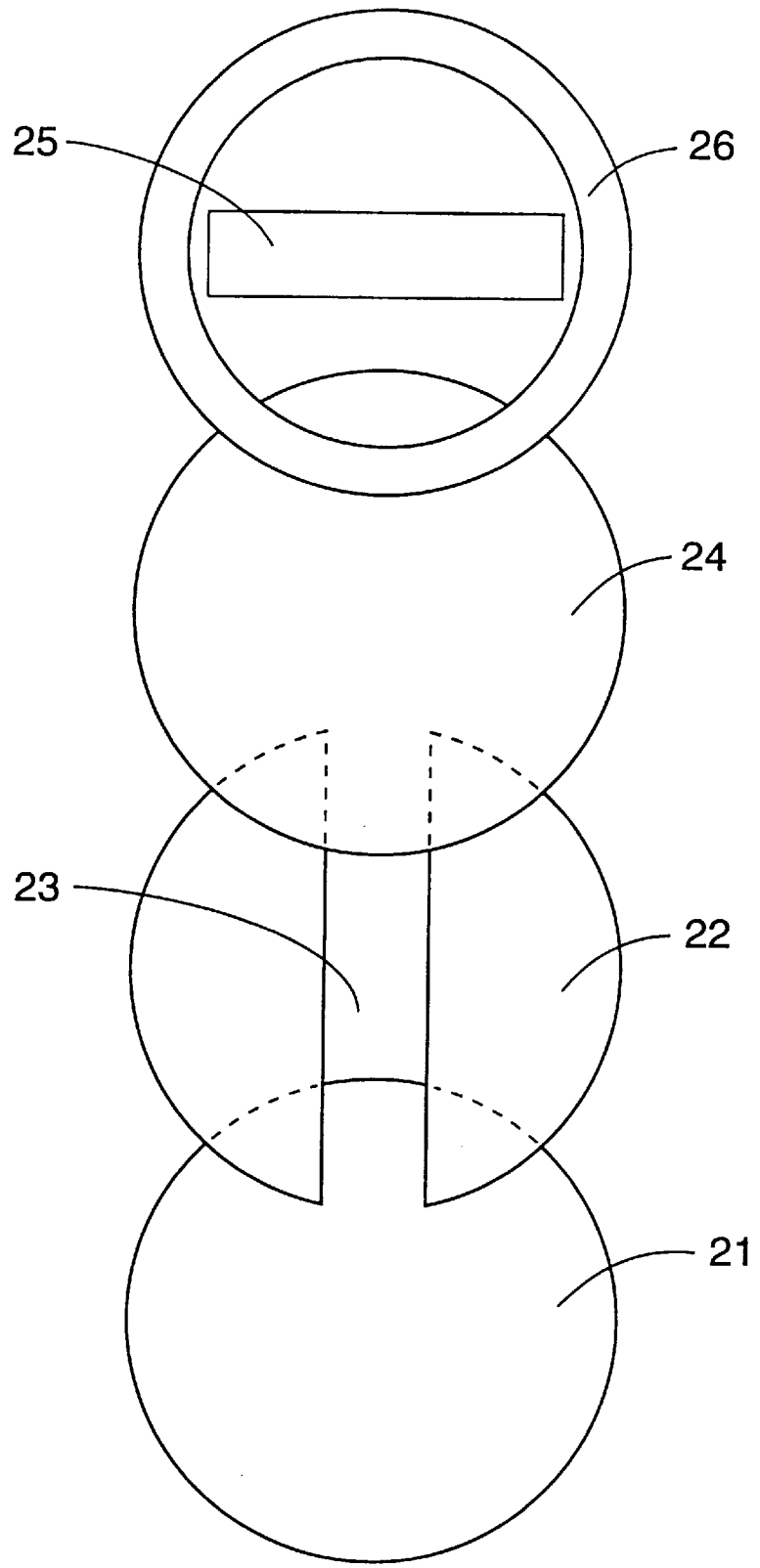
FIG. 3 is a plan view of each of several laminae in one example of an amine test element in accordance with this invention, the laminae shown separately in the order in which they are applied.
Figure 4A:
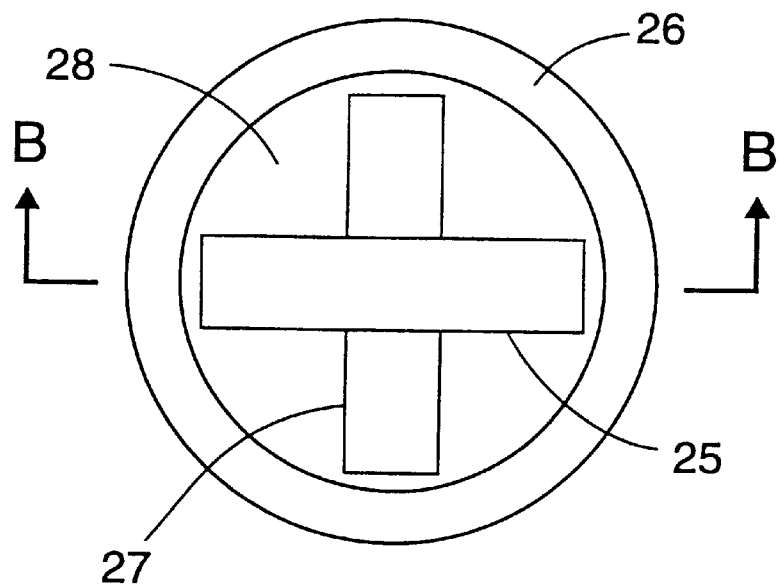
FIG. 4a is a plan view of a laminate formed from the laminae of FIG. 3.
Figure 4B:
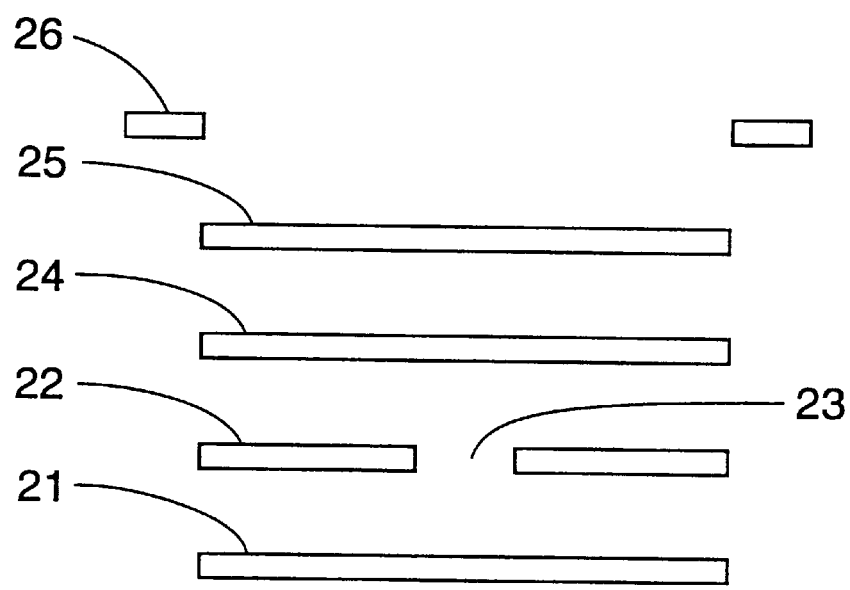
FIG. 4b is a cross section of the various laminae of FIG. 4a, taken along the line B—B thereof.

Here as well, a preferred configuration of the indicators is two crossed bars forming a plus sign. Referring to FIGS. 3, 4*a*, and 4*b*, this can be achieved with the gas-permeable indicator lamina 21 as the lower lamina, and the clear gas-channeling lamina 22 applied directly over it. An elongated gap 23 in the gas-channeling lamina divides it into two separated areas. The gap permits passage of the volatilized amines and forms the vertical bar of the plus sign. A protective liquid barrier lamina 24 (also clear) can also cover the gas-channeling lamina 22 as well as the gap 23. The positive control lamina 25 (which permits penetration by the liquid specimen) is then applied over the liquid barrier lamina 24, the positive control lamina being in the shape of a bar forming the horizontal portion of the plus sign. Finally, the gas-releasing lamina 26 is applied as a separate layer on the device, either over the protective liquid barrier 24 or outside of all of the lamina. The gas-releasing lamina in the arrangement shown in the drawing forms a ring around the horizontal bar of the positive control lamina, preferably not touching the bar. A small gap between the ring and the bar prevents a premature color change in the bar.

To use an amine test having the configuration described in the preceding paragraph, a swab moistened with vaginal fluid is wiped around the gas-releasing ring 26, then wiped across the entire circular area inside the ring, thereby contacting the positive control horizontal bar 25 and the regions above and below it. The horizontal bar 25 will change color upon contact with any specimen, and any volatile amines released by the contact of the swab with the gas-releasing ring will penetrate the liquid barrier lamina 24 and pass through the vertical bar gap 23 in the gas-channeling lamina to the gas-permeable indicator lamina 21. The color change in the latter is restricted to the region of the vertical bar 27, while the remainder of the indicator in the gas-permeable lamina (the area 28 surrounding the plus sign) is protected from the specimen and thus does not change color. Vaginal fluid specimens that do not contain volatilizable amines will thus produce a minus sign on the device (by causing a color change only in the horizontal bar 25), while specimens that do contain volatilizable amines will produce a plus sign (by causing color changes in both horizontal 25 and vertical 27 bars).

The indicators described above in connection with both the pH test and the amine test are visual indicators, yielding a color change that is detectable by the naked eye. As alternatives, this invention further contemplates machine-readable indicators, or those that become detectable upon excitation, such as fluorescence-readable indicators.

Figure 5A:
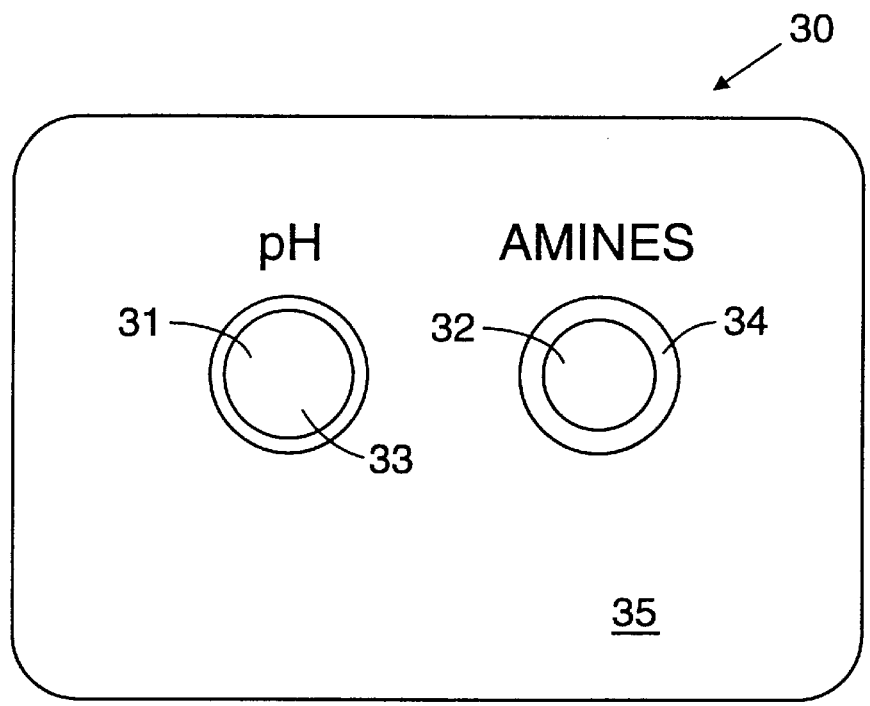
FIG. 5a is a plan view of a test card incorporating both the pH test element and the amine test element shown in the preceding figures.
Figure 5B:
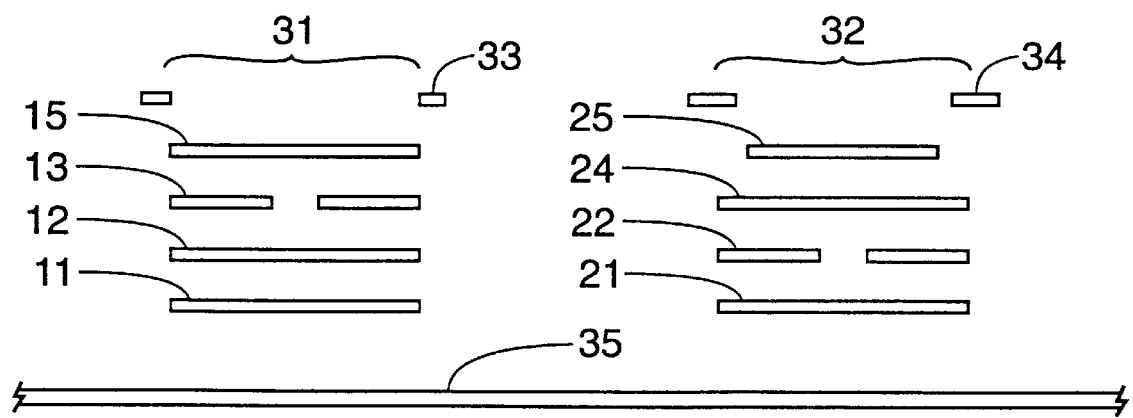

In preferred embodiments of the invention, the two tests are combined on a single test card 30 as shown in FIGS. 5*a* and 5*b*, FIG. 5*b* being an enlarged and exploded side view of FIG. 5*a*. The two tests will appear as separate areas 31, 32 on one surface of the card. Each can be outlined in a dark circle 33, 34 for enhanced visibility to the user. The dark circle 34 surrounding the amine test area can be wider since it will contain the gas-releasing lamina needed to perform the test. As shown in FIG. 5*b*, each of the test areas 31, 32 is formed of the laminates shown in the previous figures. The laminate of FIG. 2*b* is shown under test area 31, and the laminate of FIG. 4*b* is shown under test area 32, with the individual laminae identified by the same numerals used in FIGS. 2*b* and 4*b*. The card can further contain such indicia as identifying information and instructions for use. The upper surface 35 of the card can be covered with a protective sheet for protection during storage and shipping, but readily removable immediately prior to use. Application of a single biological specimen to both test areas on the card is readily accomplished by a cotton-tipped stick or any swab capable of retaining a sample and applying it to a surface. A typical test card in accordance with this invention is approximately the size of a credit card, or approximately 2 inches (5.1 cm) by 3 inches (7.6 cm) and the test areas are circular, with diameters of approximately 0.25 inch (0.635 cm).

The following examples are offered for purposes of illustration only. In these examples, test elements in accordance with the invention were used having the configurations shown in the Figures. In the pH test element, the laminae were as follows, using the reference numbers of FIG. 1:

foundation lamina 11: Mylar support with ethyl cellulose coating applied as a 15 weight percent solution of ethyl cellulose in n-propanol pH indicator lamina 12:

EUDRAGIT RL PO and nitrazine yellow applied as a solution with the following composition: 25.0% EUDRAGIT RL PO, 0.34% nitrazine yellow, 8.6% sorbitol (wetting and permeability agent, 70% aqueous solution), 10.0% 2-ethoxy ethanol, 12.4% deionized water, 43.66% 1-propanol (all by weight)

liquid-channeling barrier lamina 13: ethyl cellulose, applied as a 15% solution in 30% n-propanol (all by weight), containing a gap 14 positive control lamina 15: EUDRAGIT RL PO with nitrazine yellow and bromocresol green, applied as a solution with the following composition: 22.8% n-propanol, 12.40% deionized water, 30.00% 2-ethoxyethanol, 8.60% sorbitol (70% solution in water), 25.0% EUDRAGIT RL PO, 0.17% nitrazine yellow, 0.30% bromocresol green, and 0.65% 2-sulfobenzoic acid anhydride (for moisture resistance) (all by weight)

In the amine test element, the laminae were as follows, using the reference numbers of FIG. 3:

gas-permeable indicator lamina 21: bromocresol green in ethyl cellulose, formed from a solution of the following composition: 1.8% bromocresol green, 12% ethyl cellulose, and 86.2% n-propanol (all by weight)

gas-channeling lamina 22: clear polyamide, applied as a solution of 20% polyamide resin, 50% n-propyl acetate and 30% n-propanol (all by weight)

liquid barrier 24: ethyl cellulose applied as a solution of 10 weight percent ethyl cellulose in n-propyl alcohol positive control lamina 25: EUDRAGIT RL PO and bromocresol green applied as a solution with the following composition: 25.0% EUDRAGIT RL PO, 0.1% bromocresol green, 30.0% 2-ethoxy ethanol, 6.0% deionized water, 36.9% 1-propanol, 2.0% 2-sulfobenzoic acid anhydride (all by weight)

gas-releasing lamina 26: sodium alumina applied as a solution of 28% sodium aluminate, 18% polyethylene, 3% maltodextrin, and 51% deionized water (all by weight).

To compare these test elements with elements and procedures of the prior art, two such procedures were used. One was the use of a COLORPHAST® pH test strip, manufactured by EM Science, Gibbstown, N.J., USA, currently sold for use by physicians. The other was the whiff test referred to above in the Background of the Invention, and consisting of applying a portion of the specimen to a microscope slide, applying a drop of 10% KOH, and then performing an olfactory determination.

EXAMPLE 1

The pH test element in accordance with this invention was compared with a COLORPHAST pH test strip in performing pH tests on 607 vaginal fluid specimens.

Of the 607 specimens, 298 were negative (pH<4.7) according to the COLORPHAST test strip, and 258 of these were also negative according to the test element of this invention. This represents 86.6% negative agreement, with a standard deviation of 2.0% and a one-sided 95% confidence interval of 83.3%.

The specimens indicated by the COLORPHAST test strip as positive (pH≧4.7) numbered 309, and of these, 263 were positive as well according to the test element of this invention. This represents 85.1% positive agreement, with a standard deviation of 2.0% and one-sided 95% confidence interval of 81.8%.

Overall agreement was 85.8%, standard deviation 1.4%, and confidence interval 83.5%.

EXAMPLE 2

In this example, the Amsel criteria were used to reconcile the specimens that were not in agreement in the tests performed in Example 1. The four Amsel criteria are elevated pH, the presence of amines by the whiff test, vaginal fluid homogeneity, and the presence of clue cells. The theory behind this test is that if the vaginal fluid pH was elevated because of a vaginal infection, then at least two of the other three Amsel criteria would also be expected to be positive, in keeping with a clinical diagnosis of bacterial vaginosis (BV).

The 86 discordant samples (where one pH test showed positive and the other negative) were subjected to the remaining three Amsel criteria. Of the 40 specimens that gave negative results by the COLORPHAST test strip and positive according to the invention test strip, only two were clinically positive for BV by the Amsel criteria. Of the 46 specimens giving positive results by the COLORPHAST test strip and negative according to the invention test strip, 42 were clinically negative for BV by the Amsel criteria. This represents 98.5% positive agreement, 88.8% negative agreement and 93.1% overall agreement, using Amsel criteria to reconcile discordant results.

EXAMPLE 3

This example compares the amine test element in accordance with this invention with the whiff test. Both tests were performed on a total of 617 vaginal fluid specimens.

Of the total number of specimens tested, 196 gave a positive result by the whiff test, and of these, 166 gave a positive result as well by the test element of the invention, representing 84.7% positive agreement, a standard deviation of 2.5% and a one-sided 95% confidence interval of 80.5%.

Of the total number tested, 421 gave a negative result by the whiff test, and of these, 385 also gave a negative result by the test element of the invention, representing 91.4% negative agreement, a standard deviation of 1.4% and a one-sided 95% confidence interval of 89.2%.

Overall agreement was 89.3%, standard agreement 1.2% and a one-sided 95% confidence interval of 87.3%.

EXAMPLE 4

Amsel criteria were again used to reconcile the specimens that were not in agreement in the amine tests. Here as well, if amines were detected because of a vaginal infection, at least two of the other three Amsel criteria would be expected to be positive.

The 66 discordant amine test samples were subjected to the remaining three Amsel criteria. Positive agreement rose to 91.2%, negative agreement rose to 91.7%, and overall agreement to 91.6%.

EXAMPLE 5

This example compares the combined pH and amine tests of the present invention with the combined results of the COLORPHAST pH test strip and the standard whiff test (the reference tests). According to this test, the result using the present invention was considered positive only when both the pH and amine tests gave positive results, and the result was considered negative in all other cases, i.e., when either or both of the pH and amine tests gave a negative result. The reference tests were designated in the same manner—positive when both were positive, and negative when any one or both were negative.

Of 604 vaginal fluid specimens, 184 specimens were positive according to the reference tests, and 175 were positive according to the tests of the invention. Likewise, 420 specimens were negative according to the reference test, and 429 were negative according to the invention tests. Disagreement occurred in only 45 cases. This represents 85.3% positive agreement with standard deviation of 2.6% and a one-sided 95% confidence interval of 81.0%, 95.7% negative agreement with standard deviation of 1.0% and a one-sided 95% confidence interval of 94.1%, and 92.5% overall agreement with standard deviation of 1.1% and a one-sided 95% confidence interval of 90.8%.

EXAMPLE 6

As with the individual test elements, discrepant results between the combined tests of the invention and the combined reference tests were reconciled using the Amsel criteria to presumptively diagnose BV. Of the 18 specimens that were negative according to the combined reference tests but positive according to the combined invention tests, only two were clinically positive for BV according to the Amsel criteria. Of the 27 specimens that were positive according to the reference tests but negative according to the invention tests, ten were clinically negative for BV according to the Amsel criteria. Thus, using the Amsel criteria to reconcile the discordant test results, positive agreement rose to 90.3%, with standard deviation of 2.2% and a one-sided 95% confidence interval of 86.7%; negative agreement rose to 96.3%, with standard deviation of 0.9% and a one-sided 95% confidence interval of 94.8%, and overall agreement rose to 94.5% with standard deviation of 0.9% and a one-sided 95% confidence interval of 93.0%.

EXAMPLE 7

This example illustrates the use of the present invention in conjunction with the two additional Amsel criteria for the determination of the presence or absence of bacterial vaginosis (BV). As indicated above, diagnoses using the Amsel method are based on four criteria: (1) a pH determination, (2) a whiff test for volatile amines, (3) an examination of vaginal fluid homogeneity, and (4) a microscopic examination of vaginal fluid for the presence of clue cells. According to traditional methods of evaluating the test results, women meeting at least three of the four criteria are considered to be BV positive. First, all women in the study group were tested for all four criteria, using the COLORPHAST pH test strip for the pH test and the whiff test for the amines. The analysis was then repeated on the same group of women using the same four criteria, but substituting the pH and amine tests of the present invention for the COLORPHAST and whiff tests.

The study group consisted of vaginal specimens from 604 women. Based on the Amsel criteria using the COLORPHAST and whiff tests for the pH and amine determinations, 161 (26.6%) of the women were classified as BV positive and 443 (73.4%) were classified as BV negative. Of the 161 positives, 153 were also classified positive when the criteria were retested using the pH and amine tests of the present invention. Of the 443 negatives, 433 were also classified negative when the criteria were retested using the pH and amine tests of the present invention. This represents 95.0% positive agreement, with 1.7% standard deviation and one-sided 95% confidence interval of 92.2%. Likewise, negative agreement was 97.7%, with 0.7% standard deviation and one-sided 95% confidence interval of 96.6%. Overall agreement was 97.0%, with 0.7% standard deviation and one-sided 95% confidence interval of 95.9%; and the kappa coefficient was 0.92, with 0.02 standard deviation and one-sided 95% confidence interval of 0.90.

The 18 discordant test results were reconciled by a Gram stain test as an independent means of diagnosing BV, where a Gram stain score of 7 or above was considered BV positive. Of the 10 specimens that were BV negative by the Amsel criteria when the COLORPHAST and whiff tests were used and BV positive by the Amsel criteria when the pH and amine tests of the invention were used, 8 were clinically positive for BV by the Gram stain test. Conversely, of the 8 specimens that were BV positive by the Amsel criteria when the COLORPHAST and whiff tests were used and BV negative when the tests of the invention were used, 1 was clinically negative by the Gram test. Thus, by reconciling discordant results with the Gram stain test, positive agreement rose to 95.8%, negative agreement to 99.5%, and overall agreement to 98.5% with kappa coefficient of 0.96, standard deviation of 0.01 and one-sided 95% confidence interval of 0.94.

EXAMPLE 8

This example illustrates the use of the pH and amine tests of the present invention by themselves as test criteria for BV. Comparisons were made against the Amsel criteria (using the COLORPHAST strip for pH and the whiff test for amine), and the Gram stain test was again used to reconcile discordant results, where a Gram stain score of 7 or above was considered BV positive. For the pH and amine tests of the present invention, the diagnosis was considered positive only when both tests gave positive results. When one or both gave negative results, the diagnosis was considered negative.

Of the 607 vaginal specimens tested, 162 were positive by the Amsel criteria, and of these 162, 139 were also positive by the pH and amine tests of the invention (85.8%. standard deviation 2.7%. one-sided 95% confidence interval 81.3%). Those testing negative by the Amsel criteria were 445 in number, and of these 445, 408 (91.7%, standard deviation 1.3%, one-sided 95% confidence interval 89.5%) were also negative by the pH and amine tests of the invention. This indicates a positive predictive value of 79.0%, with standard deviation 3.1% and one-sided 95% confidence interval 73.9%; a negative predictive value of 94.7%, with standard deviation 1.1% and one-sided 95% confidence interval 92.9%; and an efficiency of 90.1%, with standard deviation 1.2% and one-sided 95% confidence interval 88.1%.

The 60 discordant test results were then reconciled with the Gram stain test. Of the 37 that were BV negative by the Amsel criteria and positive by the invention tests, 24 were clinically positive by the Gram stain. Of the 23 that were BV positive by the Amsel criteria and negative by the invention tests, 4 were clinically negative by the Gram stain.

Thus, by reconciling discordant test results with the Gram stain test, 182 specimens were BV positive by the Gram-reconciled Amsel criteria, and of these, 163 were also positive by the two tests of the invention. Similarly, 425 were negative by the Gram-reconciled Amsel criteria, and of these, 412 were also negative by the two tests of the invention. This raised positive agreement to 89.6%, with standard deviation 2.3% and one-sided 95% confidence interval 85.8%; and it raised negative agreement to 96.9%, with standard deviation 0.8% and one-sided 95% confidence interval 95.6%. These results indicate a positive predictive value of 92.6%, with standard deviation 2.0% and one-sided 95% confidence interval 89.4%; a negative predictive value of 95.6%, with standard deviation 1.0% and one-sided 95% confidence interval 94.0%; and an efficiency of 94.7%, with standard deviation 0.9% and one-sided 95% confidence interval 93.2%.

EXAMPLE 9

This example illustrates the use of the amine test of the present invention as a test for clue cells. Comparisons were made against microscopic detection of clue cells, and the Gram stain test was used to reconcile discordant results. A microscopic examination for clue cells was considered positive when clue cells constituted more than 20% of the vaginal epithelial cells present in a vaginal fluid specimen. As in the preceding examples, an amine test representing the present invention was considered positive when the amine test element produced a blue plus sign. Alternatively, the amine test representing the present invention was considered negative when the amine test element produced a blue minus sign.

Of the 625 vaginal fluid specimens tested, 167 were interpreted as positive for clue cells by microscopy. Of these 167 positive clue cell specimens, 135 were also positive by the amine test of the invention (80.8%). Specimens testing negative for clue cells by microscopy were 458 in number. Of these 458, 388 were negative by the amine test of the invention (84.7%). This indicates a positive agreement of 80.8%, a negative agreement of 84.7%, and an efficiency of 83.7%.

The 102 discordant test results were then reconciled with the Gram stain test. Of the 70 specimens that were clue cell negative by microscopy and positive by the amine test of the present invention, 36 were clinically positive for BV by Gram stain analysis. Thus, by reconciling the discordant 70 clue cell negative test results with the Gram stain, 194 specimens were clue cell positive by Gram stain-reconciled microscopy criteria, and 171 of these 194 specimens were also positive by the amine test of the invention.

Similarly, of the 32 specimens positive by the microscopy criteria and negative by the amine test of the present invention, 9 specimens were clinically negative for BV by Gram stain testing. Thus, by reconciling the discordant 32 clue cell positive test results with the Gram stain, 431 specimens were clue cell negative by Gram stain-reconciled microscopy criteria, and 397 of these 431 specimens were also negative by the amine test of the invention.

This raised the positive agreement to 88.1%, the negative agreement to 92.1%, and the overall agreement to 90.9%.

The foregoing is offered primarily for purposes of illustration. It will be readily apparent to those skilled in the art that the configurations, dimensions, reagents and other materials, procedural steps and other parameters of this invention may be further modified or substituted in various ways without departing from the spirit and scope of the invention.

What is claimed is:

1. A method for immobilizing a pH indicator containing an ionizable phenol group and a negatively charged group in a solid matrix to prevent bleeding of said indicator when wetted with an aqueous liquid sample, and for providing said indicator with a transition region of a lower pH and a narrower range of pH relative to that of said indicator when not so immobilized, said method comprising forming a solid composition comprised of said indicator dispersed in a polymer to which quaternary ammonium groups are covalently bound, with substantially no covalent bonds between said indicator and said polymer.

2. A method in accordance with claim 1 in which said pH indicator has a mid-range transition point, and said quaternary ammonium groups are present in said polymer in an amount sufficient to lower said mid-range transition point by at least about 1.0 pH unit.

3. A method in accordance with claim 1 in which said pH indicator has a mid-range transition point, and said quaternary ammonium groups are present in said polymer in an amount sufficient to lower said mid-range transition point by from about 1.0 pH unit to about 3.0 pH units.

4. A method in accordance with claim 1 in which said pH indicator has a mid-range transition point, and said quaternary ammonium groups are present in said polymer in an amount sufficient to lower said mid-range transition point by from about 1.5 pH units to about 2.5 pH units.

5. A method in accordance with claim 1 in which said pH indicator has a mid-range transition point, and said quaternary ammonium groups are present in an amount sufficient to lower said mid-range transition point by about 2.0 pH units.

6. A method in accordance with claim 1 in which said quaternary ammonium groups are present in an amount providing said polymer with an alkali value within the range of about 5 to about 50.

7. A method in accordance with claim 1 in which said quaternary ammonium groups are present in an amount providing said polymer with an alkali value within the range of about 15 to about 40.

8. A method in accordance with claim 1 in which said quaternary ammonium groups are trimethylanmmonium groups.

9. A method in accordance with claim 1 in which said polymer is an acrylic polymer.

10. A method in accordance with claim 1 in which said polymer is a copolymer of acrylic and methacrylic acid esters and said quaternary ammonium groups are trimethylammonium groups.

11. A method in accordance with claim 1 in which said negatively charged group of said pH indicator is a member selected from the group consisting of sulfate and sulfonate groups.

12. A method in accordance with claim 1 in which said pH indicator is a member selected from the group consisting of bromophenol blue, bromochlorophenol blue, bromocresol blue, bromocresol purple, nitrazine yellow, bromothymol blue, and brilliant yellow.

13. A method in accordance with claim 1 in which said pH indicator is nitrazine yellow.

* * * * *